United States Patent
Kuroda et al.

(10) Patent No.: US 11,167,016 B2
(45) Date of Patent: Nov. 9, 2021

(54) INTESTINAL FLORA IMPROVEMENT AGENT

(71) Applicants: AMANO ENZYME INC., Nagoya (JP); HIROSHIMA UNIVERSITY, Higashihiroshima (JP)

(72) Inventors: Manabu Kuroda, Kakamigahara (JP); Shotaro Yamaguchi, Kakamigahara (JP); Norihisa Kato, Higashihiroshima (JP)

(73) Assignees: AMANOENZYME INC., Nagoya (JP); HIROSHIMA UNIVERSITY, Higashihiroshima (JP)

( * ) Notice: Subject to any disclaimer, the term of this patent is extended or adjusted under 35 U.S.C. 154(b) by 345 days.

(21) Appl. No.: 15/999,357

(22) PCT Filed: Feb. 17, 2017

(86) PCT No.: PCT/JP2017/005986
§ 371 (c)(1),
(2) Date: Aug. 17, 2018

(87) PCT Pub. No.: WO2017/142080
PCT Pub. Date: Aug. 24, 2017

(65) Prior Publication Data
US 2019/0105376 A1   Apr. 11, 2019

(30) Foreign Application Priority Data
Feb. 18, 2016   (JP) .............................. JP2016-028942

(51) Int. Cl.
| *A61K 38/46* | (2006.01) |
| *A61K 38/48* | (2006.01) |
| *A61P 1/14* | (2006.01) |
| *A23L 33/17* | (2016.01) |
| *A23L 2/52* | (2006.01) |
| *A61K 36/062* | (2006.01) |
| *C12N 9/50* | (2006.01) |
| *A23L 33/10* | (2016.01) |
| *C12N 9/62* | (2006.01) |
| *A23L 29/00* | (2016.01) |
| *A23K 50/30* | (2016.01) |
| *A61P 1/10* | (2006.01) |
| *A61K 9/00* | (2006.01) |
| *C12N 9/26* | (2006.01) |
| *C12N 9/24* | (2006.01) |

(52) U.S. Cl.
CPC .............. *A61K 38/46* (2013.01); *A23K 50/30* (2016.05); *A23L 2/52* (2013.01); *A23L 29/06* (2016.08); *A23L 33/10* (2016.08); *A23L 33/17* (2016.08); *A61K 9/0053* (2013.01); *A61K 36/062* (2013.01); *A61K 38/48* (2013.01); *A61K 38/4806* (2013.01); *A61P 1/10* (2018.01); *A61P 1/14* (2018.01); *C12N 9/248* (2013.01); *C12N 9/2411* (2013.01); *C12N 9/50* (2013.01); *C12N 9/62* (2013.01); *A01K 2227/108* (2013.01); *A23V 2002/00* (2013.01)

(58) Field of Classification Search
CPC ........ A61K 38/48; A61K 9/0053; C12N 9/62; C12N 9/50; A23L 33/17
See application file for complete search history.

(56) References Cited

U.S. PATENT DOCUMENTS

| 6,042,823 A | 3/2000 | Kimura et al. |
| 2009/0155417 A1 | 6/2009 | Kadota et al. |
| 2013/0280375 A1 | 10/2013 | Kreisz et al. |
| 2013/0330307 A1 | 12/2013 | Millan |
| 2013/0330308 A1 | 12/2013 | Millan et al. |
| 2014/0234279 A1 | 8/2014 | Millan |
| 2015/0307562 A1 | 10/2015 | Basu |
| 2016/0219910 A1 | 8/2016 | Silver et al. |
| 2016/0228503 A1 | 8/2016 | Silver et al. |
| 2016/0228506 A1 | 8/2016 | Afeyan et al. |
| 2016/0317614 A1 | 11/2016 | Williams et al. |
| 2016/0339078 A1 | 11/2016 | Hamill et al. |
| 2016/0354436 A1 | 12/2016 | Williams et al. |
| 2018/0125926 A1 | 5/2018 | Williams et al. |

FOREIGN PATENT DOCUMENTS

| JP | 2000-325045 A | 11/2000 |
| JP | 2007-325580 A | 12/2007 |
| JP | 2010-004760 A | 1/2010 |
| JP | 2012-188372 A | 10/2012 |
| JP | 2014-507946 A | 4/2014 |
| WO | WO 2012/022745 A1 | 2/2012 |

(Continued)

OTHER PUBLICATIONS

Everard et al., Best Practice & Research Clinical Gastroenterology, 2013, vol. 27, p. 73-83.*
SCORE search results for SEQ ID No. 1, conducted on Jan. 22, 2021, 23 pages of PDF.*
Database Genbank [Online], "acid protease [Aspergillus oryzae].", Database accession No. BAA02994, Feb. 19, 2008.
Database Geneseq [Online], Aspergillus oryzae nutritive polypeptide, SEQ ID 4779, Database accession No. BBW96366, May 21, 2015.

(Continued)

*Primary Examiner* — Kade Ariani
(74) *Attorney, Agent, or Firm* — Knobbe, Martens, Olson & Bear LLP

(57) ABSTRACT

The purpose of the present invention is to provide an agent for improving intestinal flora which can increase the number of beneficial bacteria such as lactic acid bacteria and *Bifidobacterium* to improve intestinal flora by using an enzyme. A protease consisting of a polypeptide having an amino acid sequence shown in SEQ ID NO: 1 can increase beneficial bacteria such as lactic acid bacteria and *Bifidobacterium* in intestines to exert an excellent effect of improving intestinal flora.

2 Claims, No Drawings
Specification includes a Sequence Listing.

(56) References Cited

FOREIGN PATENT DOCUMENTS

| WO | WO 2014/081884 A1 | 5/2014 |
|---|---|---|
| WO | WO 2015/048322 A2 | 4/2015 |
| WO | WO 2015/048332 A2 | 4/2015 |
| WO | WO 2016/071989 A1 | 5/2016 |

OTHER PUBLICATIONS

Office Action dated Jul. 31, 2020 in European Application No. 17753334.6.
Effects of Aspergillus protease supplemented diets on intestinal luminal environment in rats, 68th The Japanese Society of Nutrition and Food Science Taikai Koen Yoshishu, p. 286, 3L-02a, 2014.
Gomi, K., et al., Cloning and Nucleotide Sequence of the Acid Protease-encoding Gene (pepA) from *Aspergillus oryzae*, Bioscience Biotechnology, and Biochemistry, vol. 57, No. 7, pp. 1095-1100, 1993.
International Search Report & Written Opinion, dated Apr. 25, 2017, in International Application No. PCT/JP2017/005985.
International Search Report & Written Opinion, dated Apr. 25, 2017, in International Application No. PCT/JP2017/005986.

Okazaki, Y., et al., Burdock Fermented by *Aspergillus awamori* Elevates Cecal *Bifidobacterium*, and Reduces Fecal Deoxycholic Acid and Adipose Tissue Weight in Rats Fed a High-Fat Diet, Bioscience, Biotechnology, and Biochemistry, vol. 77, No. 1, pp. 53-57, 2013.
Yang, Y., et al., Beneficial effects of protease preparations derived from *Aspergillus* on the colonic luminal environment in rats consuming a high-fat diet, Biomedical Repots, vol. 3, pp. 715-720, 2015.
Yi, J.Q., et al., The Effects of Enzyme Complex on Performance, Intestinal Health and Nutrient Digestibility of Weaned Pigs, Asian-Australasian Journal of Animal Sciences, vol. 26, No. 8, pp. 1181-1188, 2013.
Zhang, G.G., et al., Effects of dietary supplementation of multi-enzyme on growth performance, nutrient digestibility, small intestinal digestive enzyme activities, and large intestinal selected microbiota in weanling pigs, Journal of Animal Science, vol. 92, pp. 2063-2069, 2014.
Extended European Search Report, dated Sep. 10, 2019, for European Application No. 17753334.6.
Yang, Y., et al., Consumption of an acid protease derived from *Aspergillus oryzae* causes bifidogenic effect in rats, Nutrition Research, 44, pp. 60-66, 2019.

* cited by examiner

SEQUENCE LISTING

```
<160> NUMBER OF SEQ ID NOS: 5

<210> SEQ ID NO 1
<211> LENGTH: 323
<212> TYPE: PRT
<213> ORGANISM: Aspergillus oryzae

<400> SEQUENCE: 1

Ala Ser Gly His Gly Thr Val Val Thr Ser Pro Glu Pro Asn Asp Ile
1               5                   10                  15

Glu Tyr Leu Thr Pro Val Asn Ile Gly Gly Thr Thr Leu Asn Leu Asp
            20                  25                  30

Phe Asp Thr Gly Ser Ala Asp Leu Trp Val Phe Ser Glu Glu Leu Pro
        35                  40                  45

Lys Ser Glu Gln Thr Gly His Asp Val Tyr Lys Pro Ser Gly Asn Ala
    50                  55                  60

Ser Lys Ile Ala Gly Ala Ser Trp Asp Ile Ser Tyr Gly Asp Gly Ser
65                  70                  75                  80

Ser Ala Ser Gly Asp Val Tyr Gln Asp Thr Val Thr Val Gly Gly Val
                85                  90                  95

Thr Ala Gln Gly Gln Ala Val Glu Ala Ala Ser Lys Ile Ser Asp Gln
            100                 105                 110

Phe Val Gln Asp Lys Asn Asn Asp Gly Leu Leu Gly Leu Ala Phe Ser
        115                 120                 125

Ser Ile Asn Thr Val Lys Pro Lys Pro Gln Thr Thr Phe Phe Asp Thr
    130                 135                 140

Val Lys Asp Gln Leu Asp Ala Pro Leu Phe Ala Val Thr Leu Lys Tyr
145                 150                 155                 160
```

```
His Ala Pro Gly Ser Tyr Asp Phe Gly Phe Ile Asp Lys Ser Lys Phe
            165                 170                 175
Thr Gly Glu Leu Ala Tyr Ala Asp Val Asp Asp Ser Gln Gly Phe Trp
        180                 185                 190
Gln Phe Thr Ala Asp Gly Tyr Ser Val Gly Lys Gly Asp Ala Gln Lys
    195                 200                 205
Ala Pro Ile Thr Gly Ile Ala Asp Thr Gly Thr Thr Leu Val Met Leu
210                 215                 220
Asp Asp Glu Ile Val Asp Ala Tyr Tyr Lys Gln Val Gln Gly Ala Lys
225                 230                 235                 240
Asn Asp Ala Ser Ala Gly Gly Tyr Val Phe Pro Cys Glu Thr Glu Leu
                245                 250                 255
Pro Glu Phe Thr Val Val Ile Gly Ser Tyr Asn Ala Val Ile Pro Gly
            260                 265                 270
Lys His Ile Asn Tyr Ala Pro Leu Gln Glu Gly Ser Ser Thr Cys Val
        275                 280                 285
Gly Gly Ile Gln Ser Asn Ser Gly Leu Gly Leu Ser Ile Leu Gly Asp
    290                 295                 300
Val Phe Leu Lys Ser Gln Tyr Val Val Phe Asp Ser Gly Pro Arg
305                 310                 315                 320
Leu Gly Phe

<210> SEQ ID NO 2
<211> LENGTH: 17
<212> TYPE: DNA
<213> ORGANISM: Artificial Sequence
<220> FEATURE:
<223> OTHER INFORMATION: Synthetic - Forward primer for detecting
      Bifidobacterium spp.

<400> SEQUENCE: 2
cgcgtcyggt gtgaaag                                                  17

<210> SEQ ID NO 3
<211> LENGTH: 18
<212> TYPE: DNA
<213> ORGANISM: Artificial Sequence
<220> FEATURE:
<223> OTHER INFORMATION: Synthetic - Reverse primer for detecting
      Bifidobacterium spp.

<400> SEQUENCE: 3
ccccacatcc agcatcca                                                 18

<210> SEQ ID NO 4
<211> LENGTH: 22
<212> TYPE: DNA
<213> ORGANISM: Artificial Sequence
<220> FEATURE:
<223> OTHER INFORMATION: Synthetic - Forward primer for detecting
      Lactobacillus spp.

<400> SEQUENCE: 4
gaggcagcag tagggaatct tc                                            22

<210> SEQ ID NO 5
<211> LENGTH: 27
<212> TYPE: DNA
<213> ORGANISM: Artificial Sequence
<220> FEATURE:
```

```
<223> OTHER INFORMATION: Synthetic - Reverse primer for detecting
      Lactobacillus spp.

<400> SEQUENCE: 5
ggccagttac tacctctatc cttcttc                                           27
```

INTESTINAL FLORA IMPROVEMENT AGENT

PRIORITY AND CROSS REFERENCE TO RELATED APPLICATIONS

This application is a U.S. National Phase Application under 35 U.S.C. § 371 of International Application No. PCT/JP2017/005986, filed Feb. 17, 2017, designating the U.S. and published as WO 2017/142080 A1 on Aug. 24, 2017, which claims the benefit of Japanese Patent Application No. 2016-028942, filed Feb. 18, 2016. All applications for which a foreign or a domestic priority is claimed are identified in the Application Data Sheet filed herewith and are hereby incorporated by reference in their entirety under 37 C.F.R. § 1.57.

REFERENCE TO THE ELECTRONIC SEQUENCE LISTING

The present application is being filed along with an Electronic Sequence Listing as an ASCII text file via EFS-Web. The Electronic Sequence Listing is provided as a file entitled LEX024002APCSEQLIST.txt, created and last saved on Aug. 16, 2018, which is 4,049 bytes in size.

TECHNICAL FIELD

The present invention relates to an agent for improving intestinal flora which can increase the number of beneficial bacteria such as lactic acid bacteria and *Bifidobacterium* to improve intestinal flora.

BACKGROUND

Recently, causal relationships between intestinal environment and various diseases are intensively investigated to reveal that improvement of intestinal environment is effective in preventing or ameliorating various diseases. In intestine, beneficial bacteria such as lactic acid bacteria and *Bifidobacterium* and bad bacteria such as *Escherichia coli* are present in a mixed manner. Forming beneficial bacteria-dominated flora is important in order to form a healthy intestinal environment.

Conventionally, probiotics, prebiotics, and the like are developed, and various materials by which beneficial bacteria become predominant to improve intestinal flora are proposed. It is also reported that administration of digestive enzymes such as amylases and proteases can also improve intestinal flora. For example, Non-Patent Document 1 discloses that in a pig which is fed with a specific enzyme blend consisting of an amylase, a protease, and a xylanase together with animal feed, the number of *Lactobacillus* is increased and the number of *Escherichia coli* is decreased in the large intestine. Non-Patent Document 2 also discloses that in a pig which is fed with a specific enzyme blend (Nopcozyme II; Diasham Resources Pte Ltd.) consisting of an amylase derived from *Bacillus amyloliquefaciens*, a protease derived from *Bacillus subtilis*, and a xylanase derived from *Trichoderma* together with animal feed, the number of *Lactobacillus* is increased and the numbers of *Salmonella* and *Escherichia coli* are decreased.

Thus, as an enzyme preparation which can improve intestinal flora, specific enzyme blends consisting of an amylase, a protease, and a xylanase are conventionally known. However, it has not been shown that which enzyme of these enzymes contributes to the improvement of intestinal flora. Further, there is a drawback that use of such enzyme blends leads to increases in cost of producing the enzymes.

REFERENCES

Non-Patent Document 1: Yi et al., Asian Astralas. J. Anim. Sci., 2013, 26: 1181-1188
Non-Patent Document 2: Zhang et al., J. Amin. Sci., 2014, 92: 2063-2069

SUMMARY

Recently, in connection with increasing interest in health promotion, development of new materials by which beneficial bacteria become predominant to improve intestinal flora is desired. However, with respect to an agent for improving intestinal flora using an enzyme, no effective enzyme except for the conventionally reported enzyme preparations can be estimated even by analogy under the current circumstances.

Under the circumstances, an object of the present invention is to provide an agent for improving intestinal flora which can increase the number of beneficial bacteria such as lactic acid bacteria and *Bifidobacterium* to improve intestinal flora by using an enzyme.

The present inventors have made extensive investigations to solve the above problem and found that a protease consisting of a polypeptide having an amino acid sequence shown in SEQ ID NO: 1 can increase the number of beneficial bacteria such as lactic acid bacteria and *Bifidobacterium* in intestines to exert an excellent effect of improving intestinal flora. The present inventors have made further investigations based on the findings, leading to the completion of the invention.

Thus, the present invention includes the following aspects.

Item 1. An agent for improving intestinal flora comprising a protease comprising at least one of the following polypeptides (1) to (3) as an active ingredient:
(1) a polypeptide consisting of an amino acid sequence shown in SEQ ID NO: 1,
(2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
(3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1.

Item 2. A drug for oral administration for improving intestinal flora, comprising an agent for improving intestinal flora according to Item 1.

Item 3. A food additive for improving intestinal flora, comprising an agent for improving intestinal flora according to Item 1.

Item 4. Food or drink for improving intestinal flora, comprising an agent for improving intestinal flora according to Item 1.

Item 5. A method for improving intestinal flora, comprising orally applying a protease comprising at least one of the following polypeptides (1) to (3) to a person who requires improvement of intestinal flora:
(1) a polypeptide consisting of an amino acid sequence shown in SEQ ID NO: 1, (2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
(3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1.

Item 6. A protease for use in a treatment for improving intestinal flora, comprising at least one of the following polypeptides (1) to (3):
(1) a polypeptide consisting of an amino acid sequence shown in SEQ ID NO: 1,
(2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
(3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1.

Item 7. Use of a protease comprising at least one of the following polypeptides (1) to (3) for the manufacture of an agent for improving intestinal flora:
(1) a polypeptide consisting of an amino acid sequence shown in SEQ ID NO: 1,
(2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
(3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1.

The present invention can increase the number of beneficial bacteria such as lactic acid bacteria and *Bifidobacterium* and improve intestinal flora by using a specific protease, and thus is effective in forming healthy intestinal environment, maintaining healthy intestinal environment, and preventing or treating a disease and/or symptom due in part to unhealthy intestinal environment.

DETAILED DESCRIPTION

1. Agent for Improving Intestinal Flora

An agent for improving intestinal flora of the present invention is characterized by containing a specific protease as an active ingredient. The agent for improving intestinal flora of the present invention is described in detail below.

[Protease]

In the agent for improving intestinal flora of the present invention, a protease comprising at least one of the following polypeptides (1) to (3) is used as an active ingredient. By selecting and using the specific protease, beneficial bacteria such as lactic acid bacteria and *Bifidobacterium* in intestines can be increased to improve intestinal flora effectively.
(1) a polypeptide consisting of an amino acid sequence shown in SEQ ID NO: 1,
(2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
(3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1.

The polypeptide set forth in the above (1) is an acid protease derived from *Aspergillus oryzae*, and polypeptides set forth in the above (2) and (3) are variants of the polypeptide set forth in the above (1).

In the polypeptide of the above (2), amino acid modifications introduced may comprise any one of the modifications including substitution, addition, insertion, and deletion alone (e.g., substitution alone) or comprise two or more of the modifications (e.g., substitution and insertion). In the polypeptide of the above (2), the number of amino acids which is substituted, added, inserted, or deleted may be one or a few, and examples include 1 to 81, preferably 1 to 48 or 1 to 32, more preferably 1 to 16, 1 to 10, or 1 to 8, even more preferably 1 to 3, 1 or 2, or 1.

In the polypeptide of the above (3), sequence identity to the amino acid sequence shown in SEQ ID NO: 1 may be 80% or more, and is preferably 85% or more, preferably 90% or more, more preferably 95% or more, even more preferably 99% or more.

Herein, in the a polypeptide of the above (3), the sequence identity to the amino acid sequence shown in SEQ ID NO: 1 refers to a sequence identity calculated by comparison with the amino acid sequence shown in SEQ ID NO: 1. The "sequence identity" refers to a value of amino acid sequence identity obtained by bl2seq program (Tatiana A. Tatsusova, Thomas L. Madden, FEMS Microbiol. Lett., Vol. 174, p 247-250, 1999) in BLAST PACKAGE [sgi32 bit edition, Version 2.0.12; available from National Center for Biotechnology Information (NCBI)]. Parameter settings may be as follows: Gap insertion Cost value: 11 and Gap extension Cost value: 1.

In polypeptides of the above (2) and (3), when an amino acid substitution is introduced in the amino acid sequence shown in SEQ ID NO: 1, examples of the amino acid substitution introduced include a conservative substitution according to a preferred aspect. That is, examples of the substitution in the polypeptides of the above (2) and (3) include the following substitutions: when an amino acid to be substituted is a non-polar amino acid, a substitution with other non-polar amino acids; when an amino acid to be substituted is a non-charged amino acid, a substitution with other non-charged amino acids; when an amino acid to be substituted is an acidic amino acid, a substitution with other acidic amino acids; and when an amino acid to be substituted is a basic amino acid, a substitution with other basic amino acids.

In the polypeptides of the above (2) and (3), the phrase "having a protease activity equivalent to that of a polypeptide consisting of an amino acid sequence shown in SEQ ID NO: 1" refers to showing a protease activity equivalent to that of the polypeptide of the above (1) when the protease activities are measured under the following conditions (i.e., showing a protease activity of about 80 to 120% as compared to the protease activity (100%) of the polypeptide of the above (1)).

(Method for Measuring Protease Activity)

In a test tube, 5 mL of a 0.6 wt % casein solution (pH 3.0) is placed and maintained at 37° C. Then, 1 mL of an enzyme solution (in water as a solvent) containing a sample which is to be measured for a protease activity is added and allowed to stand at 37° C. for exactly 10 minutes, and then 5 mL of a 0.44 mol/L trichloroacetic acid solution is added to stop the reaction. The mixture is allowed to stand at 37° C. for 30 minutes followed by filtration with filter paper to obtain 2 mL of filtrate, which is transferred into another test tube, and then 5 mL of 0.55 mol/L sodium carbonate and 1 mL of 3-fold diluted Folin's reagent are added thereto in this order. The mixture is allowed to stand at 37° C. for 30 minutes followed by measurement of absorbance at a wavelength of 660 nm. In blank, the enzyme solution is added after the addition of the trichloroacetic acid solution. Separately, a standard curve for tyrosine is constructed using 10 to 40 μg/mL of tyrosine solutions by the same procedure as the above-described procedure for filtrate. Under the above conditions, an amount of an enzyme which causes an increase in colored materials by Folin's reagent corresponding to 1 μg of tyrosine per minute is defined as 1 U. The following equations are used for the calculation.

Protease activity per 1 g or 1 mL of sample (U/g or U/mL)=$(AT-AB) \times F \times (11/2) \times (1/10) \times 1/W$ [Equation 1]

AT: Absorbance at wavelength of 660 nm

AB: Absorbance at wavelength of 660 nm in blank

F: Amount of tyrosine (μg) corresponding to difference in absorbance of 1 as determined by standard curve for tyrosine 11/2: Factor of conversion after completion of reaction into total liquid volume 1/10: Factor of conversion into per minute of reaction W: Amount of sample (g or mL) in 1 mL of enzyme solution The polypeptide of the above (1) to (3) can be obtained by a method of culturing *Aspergillus oryzae* which produces the polypeptide, and also obtained by a publicly-known genetic engineering technique.

[Dose of Protease]

The agent for improving intestinal flora of the present invention may be applied at a suitable dose as determined according to, for example, types of products in which the agent is used, applications, expected effects, and dosage forms. Examples of a daily dose for an adult human as an amount of the above protease ingested or administered include 0.1 to 3,000 mg, preferably 1 to 2000 mg, more preferably 1 to 1000 mg, even more preferably 2 to 500 mg, still more preferably 2 to 150 mg, most preferably 5 to 100 mg.

[Use of Agent for Improving Intestinal Flora]

The agent for improving intestinal flora of the present invention can increase the number of beneficial bacteria such as *Bifidobacterium* and lactic acid bacteria in intestines by the effect of the above protease to form a beneficial bacteria-dominated flora, and thus is used for the purpose of forming healthy intestinal environment, maintaining healthy intestinal environment, and the like. Specifically, the agent for improving intestinal flora of the present invention is superior in an effect of increasing the number of bacteria of *Bifidobacterium* spp. and *Lactobacillus* spp. in intestines, and thus can also be used as an agent for increasing the number of enteric bacteria of *Bifidobacterium* spp. and *Lactobacillus* spp. in intestines.

In addition, the agent for improving intestinal flora of the present invention can form a beneficial bacteria-dominated flora to form a healthy intestinal environment, and thus can also be used for the purpose of preventing or treating a disease and/or symptom due in part to unhealthy intestinal environment. Examples of the disease and/or symptom include decreased immunity, colorectal cancer, allergic disease, nonalcoholic steatohepatitis, obesity, and inflammatory bowel disease.

[Form for Using Agent for Improving Intestinal Flora]

The agent for improving intestinal flora of the present invention is orally applied by oral ingestion or oral administration. The agent for improving intestinal flora of the present invention is orally ingested or orally administered to exert an effect of improving intestinal flora after arriving at intestines, and thus can be blended for use with various products such as food and drink, drugs for oral administration, animal feed, and pet food.

When the agent for improving intestinal flora of the present invention is blended with the above various products, the products may contain probiotics and/or prebiotics as required together with the agent for improving intestinal flora of the present invention.

Examples of a microorganism used as the probiotics include lactic acid bacteria, *Bifidobacterium*, and *Bacillus subtilis* var natto. Specific examples of the lactic acid bacteria include lactic acid bacteria of *Lactobacillus* spp. such as *Lactobacillus casei, Lactobacillus acidophilus*, and *Lactobacillus plantarum*; lactic acid bacteria of *Enterococcus* spp. such as *Enterococcus faecalis, Enterococcus faecium*, and *Enterococcus hirae*; and lactic acid bacteria of *Streptococcus* spp. such as *Streptococcus bovis* and *Streptococcus thermophilus*. Specific examples of *Bifidobacterium* include *Bifidobacterium adolescentis, Bifidobacterium longum, Bifidobacterium bifidum, Bifidobacterium pseudolongum*, and *Bifidobacterium thermophilum*. These probiotics may be used alone or in combination of two or more.

Examples of the prebiotics include xylooligosaccharide, fructooligosaccharide, soybean oligosaccharides, isomaltooligosaccharide, lacto-fructo-oligosaccharides, galactooligosaccharides, and lactulose. These prebiotics may be used alone or in combination of two or more.

A formulation of a product with which the agent for improving intestinal flora of the present invention is blended may be any one of solid form, semi-solid form, liquid form, and the like, and is suitably selected according to types and applications of the product.

When the agent for improving intestinal flora of the present invention is used for food and drink, the above protease is provided, as food and drink for improving intestinal flora, solely or in combination with other food materials or additives to be prepared in a desired form. Examples of the food and drink include a food for specified health uses, a nutritional supplement, a functional food, and a food for patients in addition to common food and drink. Forms of these foods and drinks are not specifically limited. Specific examples include supplements such as tablets, granules, powders, capsules, and soft capsules; and drinks such as energy drinks, fruit drinks, carbonated beverages, and lactic acid drinks.

When the agent for improving intestinal flora of the present invention is used for food and drink, an amount of the agent blended into the food and drink varies according to, for example, forms of the food and drink. In supplements, the agent may be blended, for example, so that an amount of the above protease is in a range of 0.03 to 1,000 mg/g, preferably 0.3 to 700 mg/g, more preferably 0.3 to 350 mg/g, even more preferably 0.6 to 170 mg/g, still more preferably 0.6 to 80 mg/g, most preferably 1.5 to 50 mg/g. In drinks, the agent may be blended, for example, so that an amount of the above protease is in a range of 0.0003 to 10 mg/mL, preferably 0.003 to 7 mg/mL, more preferably 0.003 to 3.5 mg/mL, even more preferably 0.006 to 1.7 mg/mL, still more preferably 0.006 to 0.8 mg/mL, most preferably 0.015 to 0.5 mg/mL.

When the agent for improving intestinal flora of the present invention is used in the food and drink field, the agent for improving intestinal flora of the present invention can be provided, as a food additive, solely or in combination with other ingredients.

When the agent for improving intestinal flora of the present invention is used for drugs for oral administration, the agent for improving intestinal flora of the present invention is provided, as drugs for oral administration which exert an effect of improving intestinal flora, solely or in combination with, for example, other pharmacologically active ingredients, pharmaceutically acceptable bases, or additives to be prepared in a desired form. Forms of the drugs are not specifically limited. Specific examples include formulations for oral administration such as tablets, granules, powders, capsules, soft capsules, syrups, and liquids.

Examples of the bases and the additives used for manufacturing the drugs for oral administration include aqueous bases such as water and alcohol, oil-based bases, diluents, binders, filling agents, disintegrants, lubricants, algefacients, pH-adjusting agents, thickeners, antioxidants, sequestering agents, surfactants, emulsifiers, solubilizers, solubilizing agents, flavoring agents, and antiseptics.

When the agent for improving intestinal flora of the present invention is used as drugs for oral administration, ratio of the agent blended into the drugs for oral administration can be suitably determined according to, for example, forms of the drugs for oral administration within a range satisfying the above described dose. In drugs for oral administration in solid form or semi-solid form, the agent may be blended, for example, so that an amount of the above protease is in a range of 0.03 to 1,000 mg/g, preferably 0.3 to 700 mg/g, more preferably 0.3 to 350 mg/g, even more preferably 0.6 to 170 mg/g, still more preferably 0.6 to 80 mg/g, most preferably 1.5 to 50 mg/g. In drugs for oral administration in liquid form, the agent may be blended, for example, so that an amount of the above protease is in a range of 0.0003 to 10 mg/mL, preferably 0.003 to 7 mg/mL, more preferably 0.003 to 3.5 mg/mL, even more preferably 0.006 to 1.7 mg/mL, still more preferably 0.006 to 0.8 mg/mL, most preferably 0.015 to 0.5 mg/mL.

When the agent for improving intestinal flora of the present invention is used for animal feed or pet food, the agent for improving intestinal flora of the present invention is provided, as animal feed or pet food which exerts an effect of improving intestinal flora, solely or in a desired form controlled in combination with other animal feed ingredients. Examples of the animal feed ingredients used for animal feed or pet food include cereal crops such as corn, wheat, barley, and rye; brans such as wheat bran and rice bran; dregs such as corn gluten meal and corn germ meal; animal-derived feed such as skimmed milk powder, whey, fish flour, and powdered bone; yeasts such as brewer's yeast; calciums such as calcium phosphate and calcium carbonate; vitamins; amino acids; and saccharides.

When the agent for improving intestinal flora of the present invention is used as animal feed or pet food, ratio of the agent blended into the animal feed or pet food varies according to, for example, forms and types of the animal feed or pet food, and types of animals for application. For example, the agent may be blended so that an amount of the above protease is in a range of 0.00067 to 6.7 mg/g, preferably 0.0067 to 6.7 mg/g, more preferably 0.0067 to 0.67 mg/g.

2. Other Aspects

As described above, the above-described protease has an effect of improving intestinal flora. Thus, the present invention further provides a method for improving intestinal flora comprising orally applying the above-described protease to a person who requires improvement of intestinal flora, the above-described protease for use in a treatment for improving intestinal flora, and use of the above-described protease for the manufacture of an agent for improving intestinal flora. The above specific aspects of the present invention are as described in the above section of "1. Agent for improving intestinal flora".

EXAMPLE

The present invention is described more specifically below with reference to Example, but it should not be construed to be limited to the example.

Test Example 1: Influence of Polypeptide Consisting of an Amino Acid Sequence Shown in SEQ ID NO: 1 on Intestinal Flora 1. Preparation of Protease A protease comprising a polypeptide consisting of an amino acid sequence shown in SEQ ID NO: 1 was prepared from a koji extract obtained by culturing a microorganism which is a strain producing the protease by a solid-state fermentation. Specifically, *Aspergillus oryzae* was cultured on a solid culture medium comprising wheat bran at 25±5° C. for 3 days. The koji after the culturing was immersed in water to extract the polypeptide, followed by removal of the koji by filtration through diatomaceous earth to obtain a polypeptide solution. Then, the polypeptide solution was concentrated by using ultra filtration membrane, followed by desalting to obtain a partial purified polypeptide solution. The partial purified polypeptide solution was sterilized by filtration through a membrane filter, followed by spray drying using a spray dryer to give a power of a partially purified polypeptide. The partially purified polypeptide was subjected to a purification step comprising ion exchange column chromatography, hydrophobic column chromatography, gel filtration chromatography, desalting column chromatography, and freeze-drying in this order to yield a powder of a purified polypeptide. The resulting purified polypeptide was subjected to SDS-polyacrylamide gel electrophoresis and CBB staining to detect a band of the polypeptide, which was treated with an enzyme followed by LC-MS/MS analysis and was confirmed to be a polypeptide consisting of an amino acid sequence shown in SEQ ID NO: 1.

2. Evaluation of Effect of Improving Intestinal Flora Using Rat

Using SD rats (male, 3 weeks old, from Hiroshima Institute for Experimental Animals), an influence of ingestion of a protease comprising a polypeptide having an amino acid sequence shown in SEQ ID NO: 1 on intestinal flora was investigated. In the experiment, the rats were divided into 4 groups consisting of control groups 1 and 2 and working groups 1 and 2, and the number of rats in each group was as follows: control group 1: 8 rats, control group 2: 4 rats, working group 1: 4 rats, and working group 2: 4 rats. The rats of each group were fed ad libitum for 14 days with animal feeds shown in Table 1.

TABLE 1

| Ingredient | Control group 1 % w/w | Working group 1 % w/w | Working group 2 % w/w | Control group 2 % w/w |
| --- | --- | --- | --- | --- |
| Beef tallow | 30.00 | 30.00 | 30.00 | 30.00 |
| Casein | 20.00 (Net protein: 17.40) | 20.00 (Net protein: 17.40) | 20.00 (Net protein: 17.40) | 20.00 (Net protein: 17.40) |

TABLE 1-continued

| Ingredient | Control group 1 % w/w | Working group 1 % w/w | Working group 2 % w/w | Control group 2 % w/w |
|---|---|---|---|---|
| L-Cysteine | 0.30 | 0.30 | 0.30 | 0.30 |
| Cellulose | 5.00 | 5.00 | 5.00 | 5.00 |
| Vitamin Mix #1 | 1.00 | 1.00 | 1.00 | 1.00 |
| Mineral Mix #1 | 3.50 | 3.50 | 3.50 | 3.50 |
| Sucrose | 20.00 | 20.00 | 20.00 | 20.00 |
| Corn starch | 20.20 | 20.1904 | 20.1616 | 20.1616 |
| Polypeptide #2 | — | 0.0096 | 0.0384 | — |
| Inactivated polypeptide #3 | — | — | — | 0.0384 |

1 refers to a standard purified diet for mice and rats according to AIN-93 (American Institute of Nutrition (AIN)).
2 refers to a protease consisting of a polypeptide of an amino acid sequence shown in SEQ ID NO: 1.
3 refers to a polypeptide, which is a polypeptide of an amino acid sequence shown in SEQ ID NO: 1 inactivated under conditions of the trichloroacetic acid treatment.

Bacteria in cecal contents of the SD rats were analyzed after 14-day feeding with the animal feed by real-time PCR using primers shown in Table 2 to calculate the numbers of Bifidobacterium (Bifidobacterium spp.) and lactic acid bacteria (Lactobacillus spp.) in intestines.

TABLE 2

| | Base sequences of primers used |
|---|---|
| For detecting Bifidobacterium spp. | Forward: CGCGTCYGGTGTGAAAG (SEQ ID NO: 2)<br>Reverse: CCCCACATCCAGCATCCA (SEQ ID NO: 3) |
| For detecting Lactobacillus spp. | Forward: GAGGCAGCAGTAGGGAATCTTC (SEQ ID NO: 4)<br>Reverse: GGCCAGTTACTACCTCTATCC TTCTTC (SEQ ID NO: 5) |

3. Results

The results are shown in Table 3. In the working groups 1 and 2, the numbers of Bifidobacterium and lactic acid bacteria in intestines were both higher than those in the control groups 1 and 2. That is, it was confirmed that ingestion of the protease having the amino acid sequence shown in SEQ ID NO: 1 promoted proliferations of Bifidobacterium and lactic acid bacteria, leading to improvement of intestinal flora. It was also confirmed that ingestion of a protease having an enzyme activity, which is not merely an administration of a peptide, improved intestinal flora.

TABLE 3

| | | Control group 1 | Working group 1 | Working group 2 | Control group 2 |
|---|---|---|---|---|---|
| Intestinal flora (% of total bacteria) | Bifidobacterium spp. | 0.001 ± 0.000 | 0.282 ± 0.045 | 1.826 ± 0.214 | 0.005 ± 0.002 |
| | Lactobacillus spp. | 0.90 ± 0.21 | 2.85 ± 0.68 | 3.05 ± 0.60 | 1.21 ± 0.53 |

What is claimed is:

1. A method for improving intestinal flora, comprising orally administering a protease comprising at least one of the following polypeptides (1) to (3) to a person who requires improvement of intestinal flora:
   (1) a polypeptide consisting of an amino acid sequence shown in SEQ ID NO: 1,
   (2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
   (3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1 wherein the protease increase the number of Bifidobacteria and Lactic add bacteria in intestines of said subject, thereby improves the intestinal flora.

2. A method of treatment for improving intestinal flora comprising administering a protease comprising at least one of the following polypeptides (1) to (3) to a person who requires improvement of intestinal flora:
   (1) a polypeptide consisting of an amino acid sequence shown in SEQ ID NO: 1,
   (2) a polypeptide comprising an amino acid sequence in which one or a few amino acids are substituted, added, inserted, or deleted in the amino acid sequence shown in SEQ ID NO: 1, and having a protease activity equivalent to that of a polypeptide consisting of an amino acid sequence shown in SEQ ID NO: 1, and
   (3) a polypeptide comprising an amino acid sequence having 80% or more sequence identity to an amino acid sequence shown in SEQ ID NO: 1, and having a protease activity equivalent to that of a polypeptide consisting of an amino acid sequence shown in SEQ ID NO: 1 wherein the protease increase the number of Bifidobacteria and Lactic add bacteria in intestines of said subject, thereby improves the intestinal flora.

\* \* \* \* \*